(12) United States Patent
Choi

(10) Patent No.: US 12,239,439 B2
(45) Date of Patent: Mar. 4, 2025

(54) APPARATUS AND METHOD FOR OBESITY PREVENTION AND WEIGHT REGULATION USING NONINVASIVELY MEASURING BLOOD SUGAR

(71) Applicant: MyoungSeok Choi, Seoul (KR)

(72) Inventor: MyoungSeok Choi, Seoul (KR)

(*) Notice: Subject to any disclaimer, the term of this patent is extended or adjusted under 35 U.S.C. 154(b) by 0 days.

(21) Appl. No.: 17/715,058

(22) Filed: Apr. 7, 2022

(65) Prior Publication Data
US 2023/0301554 A1 Sep. 28, 2023

(30) Foreign Application Priority Data
Mar. 28, 2022 (KR) .................. 10-2022-0037938

(51) Int. Cl.
| | | |
|---|---|---|
| A61B 5/145 | (2006.01) | |
| A61B 5/11 | (2006.01) | |
| G16H 50/30 | (2018.01) | |
| G16H 50/70 | (2018.01) | |
| A61B 5/00 | (2006.01) | |
| A61B 5/024 | (2006.01) | |

(52) U.S. Cl.
CPC ......... *A61B 5/14532* (2013.01); *G16H 50/30* (2018.01); *G16H 50/70* (2018.01); *A61B 5/0075* (2013.01); *A61B 5/02416* (2013.01); *A61B 5/1118* (2013.01); *A61B 5/4866* (2013.01); *A61B 5/7275* (2013.01); *A61B 2562/0219* (2013.01)

(58) Field of Classification Search
CPC ............. A61B 5/14532; A61B 5/0075; A61B 5/02416; A61B 5/1118; A61B 5/7275; A61B 2562/0219; G16H 50/30; G16H 50/70
See application file for complete search history.

(56) References Cited

U.S. PATENT DOCUMENTS

| | | | |
|---|---|---|---|
| 2003/0208113 A1* | 11/2003 | Mault | G16H 40/63 600/316 |
| 2005/0113650 A1* | 5/2005 | Pacione | A61B 5/4866 600/300 |
| 2016/0328991 A1* | 11/2016 | Simpson | G09B 19/0092 |
| 2017/0273610 A1* | 9/2017 | Suri | A61B 5/15105 |
| 2021/0267506 A1* | 9/2021 | Selander | A61B 5/7475 |

FOREIGN PATENT DOCUMENTS

KR 10-2326690 B1 11/2021

OTHER PUBLICATIONS

Casey Means, MD, "What should your glucose levels be? Here's the ultimate guide to healthy blood sugar ranges.", levelshealth.com, p. 1-14 (Year: 2020).*

\* cited by examiner

*Primary Examiner* — Alex M Valvis
*Assistant Examiner* — Kyle W. Kretzer
(74) *Attorney, Agent, or Firm* — Revolution IP, PLLC

(57) ABSTRACT

The present invention is to provide an apparatus and a method for obesity prevention and weight regulation, which can efficiently regulate and manage gaining and losing weight by maintaining a blood sugar level suitable for a personal situation through regulation of eating food and activity regulation by using a blood sugar value measured using noninvasively measuring blood sugar.

3 Claims, 3 Drawing Sheets

APPARATUS AND METHOD FOR OBESITY PREVENTION AND WEIGHT REGULATION USING NONINVASIVELY MEASURING BLOOD SUGAR

TECHNICAL FIELD

The present invention relates to an apparatus and a method for obesity prevention and weight regulation, and particularly, to an apparatus and a method for obesity prevention and weight regulation, which can efficiently regulate and manage gaining and losing weight by maintaining a blood sugar level suitable for a personal situation through regulation of eating food and activity regulation by using a blood sugar value measured using noninvasively measuring blood sugar.

BACKGROUND ART

In a modern society, while there are a lot of people who want weight losing due to obesity and overweight due to heavy drinking, excessive eating, etc., westernization of a dietary life, insufficient exercise, excessive stress, etc., at the same time, there are just as many people, going through rapid weight losing by the sequalae wasting disease or cancer treatment, who want to properly gain weight etc., but it is difficult to gain weight, and as a result, there are many cases in which a health cannot be restored.

In such opposite situations of desiring weight loss and gain, various attempts including dietary control, exercise, drug, and etc., are made but immoderate measures only worsen one's health state and unsatisfying results ensue, hence often being unsustainable.

Further, despite being in a standard weight range, when one's weight is remarkably increased during the age of 18 to 20, there is a shocking report that the odds of developing diabetes, gout, liver disease, and etc., are approximately 40% higher, implying that being in a standard weight range is not any safer.

Likewise, a conventional view on obesity prevention and weight regulation has a problem in that they are managed solely based on simple weight loss and gain and obesity rate through a body fat ratio. This causes a lot of side effects and is not efficient.

Although there are notable technological advancements in current medicine, weight change and obesity having multi-factorial backgrounds cannot be easily solved with the conventional view. Therefore, it is known that obesity prevention and weight regulation based on fundamental evidence-based science are urgent and can be achieved through improvement of a dietary pattern and a life style modification such as exercise,

PRIOR ART DOCUMENT

Patent Document (Patent Document 1) Korean Patent Registration No. 10-2304563 (Registered on Sep. 15, 2021)
(Patent Document 2) Korean Patent Registration No. 10-2326690 (Registered on Nov. 10, 2021)

DISCLOSURE

Technical Problem

The present invention is contrived to solve the above problem with the object to provide an apparatus and a method for obesity prevention and weight regulation, which can efficiently adjust and manage gaining and losing weight by maintaining a blood sugar level suitable for a personal situation through regulation of eating food and activity regulation by using a blood sugar value measured using noninvasively measuring blood sugar.

The object of the present invention is to provide an apparatus and a method for obesity prevention and weight regulation which facilitate management of regulation of intake food and activity control by checking a blood sugar measured and displayed in real time using noninvasvely measuring blood sugar.

The object of the present invention is to provide an apparatus and a method for obesity prevention and weight regulation, which are capable of managing weight regulation and obesity prevention through improvement of a dietary life and improvement of a life style such as exercise, etc., by displaying a blood sugar level signal for each individual based on a blood sugar amount measured in real time through a wearable device of an each individual.

The objects of the present invention are not limited to the above-mentioned objects, and other objects and advantages of the present invention that are not mentioned can be understood by the following description, and will be more clearly understood by embodiments of the present invention. Further, it will be readily appreciated that the objects and advantages of the present disclosure can be realized by means and combinations shown in the claims.

Technical Solution

In order to achieve the above object, an apparatus for obesity prevention and weight regulation using noninvasively measuring blood sugar is characterized to include: a sensing unit sensing motion sensing information and body information to generate life pattern bio information; a storage unit storing the life pattern bio information including the motion sensing information and the body information generated by the sensing unit, storing motion standard model information to be compared so as to judge a state of the user by comparing with the motion sensing information, and storing blood sugar amount measurement information including an acquired blood sugar amount measurement value, and blood sugar amount integrated information to be compared so as to judge a blood sugar level corresponding to weight gaining or losing for each user by comparing the blood sugar amount measurement information; a blood sugar measurement unit measuring a blood sugar amount in real time through noninvasive blood sugar measurement to acquire the blood sugar amount measurement information; a personal matching unit comparing the blood sugar amount measured by the blood sugar measurement unit with the blood sugar amount integrated information stored in the storage unit based on a range of a blood level, and increase and decrease information, which are input externally or are predetermined; a blood sugar level processing unit outputting a personal matching result in real time by using a comparison result of the personal matching unit; and an output unit outputting the personal matching result output by the blood sugar level processing unit to the outside to be recognized externally.

In order to achieve the above object, a method for obesity prevention and weight regulation using noninvasively measuring blood sugar is characterized to include: (A) sensing motion sensing information and body information by using a sensing unit, and associating the information with visual information to generate life pattern bio information; (B)

measuring a blood sugar amount in real time through noninvasive blood sugar measurement by using a blood sugar measurement unit to acquire blood sugar amount measurement information; (C) comparing the blood sugar amount measured by the blood sugar measurement unit 40 with blood sugar amount integrated information stored in the storage unit 20 based on a range of a blood level, and increase and decrease information, which are input by a user or are predetermined by using a personal matching unit; (D) outputting a personal matching result in real time by using a comparison result of the personal matching unit by using a blood sugar level processing unit; and (E) outputting the output matching result to the outside to be recognized externally by using an output unit.

Preferably, step (D) may include a first judgment step of judging to which state or situation the motion of the user corresponds by comparing the motion sensing information sensed by the sensing unit with predetermined motion standard model information, a second judgment step of judging whether a health state or a specific situation of the user corresponds to a specific state by comparing the bio information sensed by the sensing unit and predetermined bio information standard model information with each other, and as results of the first and second judgments, generating life pattern regulation information corresponding to the judged state information of the user.

Advantageous Effects

As described above, an apparatus and a method for obesity prevention and weight regulation using noninvasively measuring blood sugar according to the present invention provide the following effects.

First, it is possible to efficiently regulate and manage gaining and losing weight by maintaining a blood sugar level suitable for a personal situation through regulation of eating food and activity regulation by using a blood sugar value measured using noninvasively measuring blood sugar.

Second, it is possible to reduce a side effect which occurs in obesity prevention and weight regulation with management of regulation of intake food and activity control by checking a blood sugar measured and displayed in real time using noninvasively measuring blood sugar.

Third, it is possible to manage weight regulation and obesity prevention through improvement of a dietary life and improvement of a life style such as exercise, etc., by displaying a blood sugar level signal for each individual based on a blood sugar amount measured in real time through a wearable device worn on a body of a user, thereby giving convenience and easiness for management.

In addition to the above-described effects, the specific effects of the present invention will be described below together while describing the specific matters for the present invention.

MODES FOR THE INVENTION

Other objects, characteristics, and advantages of the present invention will become apparent through the detailed description of the embodiments referred to in the accompanying drawings.

Terms used in the present invention adopt general terms which are currently widely used as possible by considering functions in the present invention, but the terms may be changed depending on an intention of those skilled in the art, a precedent, emergence of new technology, etc. Further, in a specific case, a term which an applicant arbitrarily selects is present and in this case, a meaning of the term will be disclosed in detail in a corresponding description part of the invention. Accordingly, a term used in the present invention should be defined based on not just a name of the term but a meaning of the term and contents throughout the present invention.

Further, throughout the specification, unless explicitly described to the contrary, the word "comprise" and variations such as "comprises" or "comprising", will be understood to imply the inclusion of stated elements but not the exclusion of any other elements. In addition, terms including "part", "module", and the like disclosed in the specification mean a unit that processes at least one function or operation and this may be implemented by hardware or software or a combination of hardware and software.

Preferred embodiments of an apparatus and a method for obesity prevention and weight regulation using noninvasively measuring blood sugar according to the present invention will be described below with reference to the accompanying drawings. The present invention is not limited to an embodiment disclosed below but may be implemented in various different shapes and the present embodiment just completes a disclosure of the present invention and is provided to completely inform a scope of the present invention to those skilled in the art. Accordingly, configurations illustrated in the embodiments and drawings disclosed in the present specification are only the most preferred embodiment of the present invention and do not represent all of the technical spirit of the present invention, and thus it is to be understood that various equivalents and modified examples, which may replace the configurations, are possible when filing the present application.

Further, when it is disclosed that any component is "connected", "coupled", or "linked" to other components, it should be understood that the components may be directly connected or linked to each other, but another component may be "interposed" between the respective components or the respective components may be "connected", "coupled", or "linked" through another component.

Figure 1:
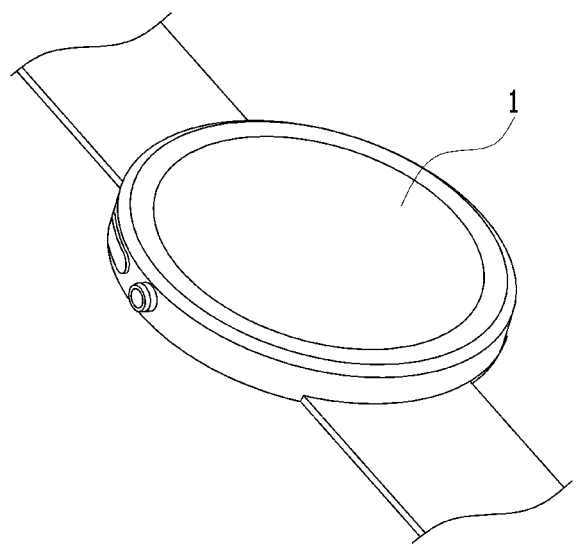
FIGS. 1 and 2 are diagrams illustrating an apparatus for obesity prevention and weight regulation using noninvasively measuring blood sugar according to an embodiment of the present invention.
Figure 2:
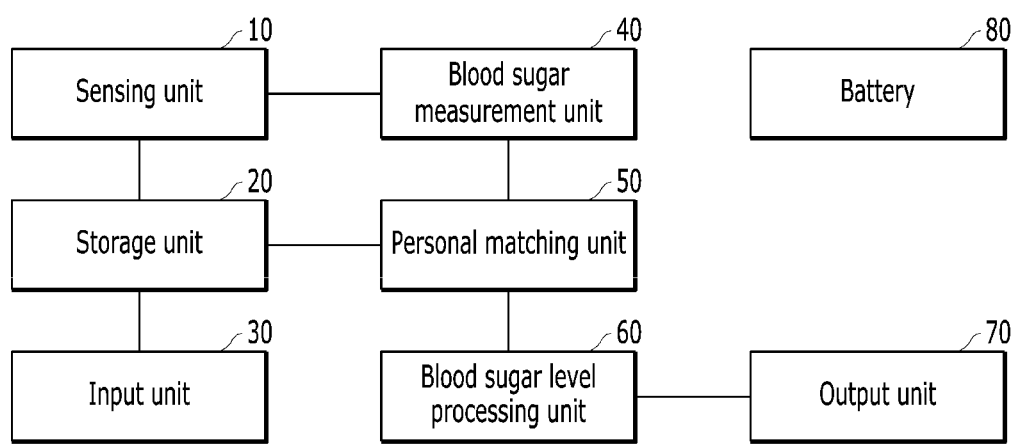

FIGS. 1 and 2 are diagrams illustrating an apparatus for obesity prevention and weight regulation using noninvasively measuring blood sugar according to an embodiment of the present invention. However, components of an apparatus for obesity prevention and weight regulation using noninvasively measuring blood sugar illustrated in FIG. 2 follows the embodiment, and it should be noted that constituent elements thereof are not limited to the embodiment illustrated in FIG. 2 and as necessary, some constituent elements may be added, modified, or deleted.

As illustrated in FIG. 1, the apparatus 1 for obesity prevention and weight regulation according to the present invention may be configured in a form of a wearable device worn on a body of a user, such as a smart watch which is a wrist wearing type.

In addition, as illustrated in FIG. 2, the apparatus 1 for obesity prevention and weight regulation according to the present invention may include a sensing unit 10, a storage unit 20, an input unit 30, a blood sugar measurement unit 40 a personal matching unit 50, a blood sugar level processing unit 60, an output unit 70, and a battery unit 80.

The sensing unit 10 senses motion sensing information and body information, and associates the information with visual information to generate life pattern bio information. In this case, the motion sensing information as information acquired by sensing a motion of a user's arm by using a gyro or acceleration sensor is information through which an activity depending on a physical motion of the user, such as eating, sleeping, or exercise may be judged. Further, the body information as information acquired by sensing a body temperature, a heart rate, blood oxygen saturation, etc., of the user by using a heart rate pulse sensor, a body temperature sensor, a blood oxygen saturation sensor, a GPS sensor, etc., refers to information regarding a health state of the body.

As an example, the life pattern bio information may include light RAM sleep, deep sleep, heart rate information including a heart rate per time, blood oxygen saturation, the body temperature of the user, a food intake amount, etc., generated through the body information in addition to going to bed, wake-up, eating start, eating end, motion start depending on movement, motion end depending on movement, a movement distance, a movement velocity, the number of walks, etc., jointly with the visual information.

To this end, the sensing unit 10 may include various sensors. As an example, the sensing unit 10 may include the heart rate pulse sensor, the gyro sensor, the acceleration sensor, the body temperature sensor, the blood oxygen saturation sensor, the GPS sensor, etc. Therefore, the heart rate pulse sensor provided to acquire the bio information of the user is acquired by sensing heart rate information for a heart rate state of the user like the heart rate. In addition, the blood oxygen saturation sensor acquires blood oxygen saturation information by measuring the blood oxygen saturation of the user. Further, the GPS sensor announces a current location of the user, and acquires tracking information such as the movement distance and the movement velocity, the number of walks, etc., by tracking total movement distance information for one day.

The storage unit 20 stores the life pattern bio information including the motion sensing information and the body information generated by the sensing unit 10, stores motion standard model information to be compared so as to judge a state of the user by comparing with the motion sensing information, and stores blood sugar amount measurement information including a blood sugar amount measurement value acquired by the blood sugar measurement unit 40, and blood sugar amount integrated information to be compared so as to judge a blood sugar level corresponding to weight gaining or losing for each user by comparing the blood sugar amount measurement information.

In respect to the blood sugar amount integrated information, a blood sugar level at which the weight is lost is set to 70 mg/dl or more to less than 100 mg/dl based on fasting blood sugar and a blood sugar level at which the weight is not significantly gained after eating is set to 100 mg/dl or more to less than 140 mg/dl. In addition, a blood sugar level at which a large weight may be gained may be defined to be 140 mg/dl or more, and when the corresponding blood sugar level is 200 mg/dl or more, there may be a possibility of diabetes.

The input unit 30 receives predetermined information from the user so as for the user to selectively set a range of the blood sugar level with respect to the personal blood sugar amount integrated information stored in the storage unit 20 or input increase and decrease information for selecting and regulating gaining or losing the weight. In this case, when the input unit 30 is the wrist wearing type, the input unit 30 may be provided in a form such as button type switches configured on both lateral surfaces or a touch pad on a display.

The blood sugar measurement unit 40 acquires the blood sugar amount information measuring the blood sugar amount of the user in real time using noninvasively measuring blood sugar. In this case, the blood sugar amount measurement information as information acquired by measuring the blood sugar amount of the user by the blood sugar measurement unit 40 refers to information including a blood sugar measurement time and a blood sugar amount measurement value. The blood sugar measurement unit 40 associates the blood sugar amount measurement value acquired through the measurement with the blood sugar measurement time to generate the blood sugar amount measurement information. Here, the blood sugar measurement time refers to a time of measuring the blood sugar amount.

When the blood sugar measurement unit 40 is the wrist wearing type, the blood sugar amount may be measured by a non-contact scheme such as a Raman spectrometer, an ultra-electromagnetic wave, or infrared rays for the blood sugar saturation at a wrist portion. The Raman spectrometer is a device called 'smart watch type blood sugar meter' because the Raman spectrometer is developed as a core component of a wrist clock type noninvasive blood sugar measuring instrument which has being studied in recent years, and as a result, the Raman spectrometer may be easily worn and may conveniently measure the blood sugar. Likewise, the blood sugar measurement unit 40 is not limited to any one component, and may adopt a measurement instrument that measures the blood sugar amount by various non-contact schemes.

The personal matching unit 50 compares the blood sugar amount measured by the blood sugar measurement unit 40 with the blood sugar amount integrated information stored in the storage unit 20 based on a range of a blood level, and increase and decrease information, which are input by the input unit 30 or are predetermined.

The blood sugar level processing unit 60 output a user-specific matching result in real time by using a matching result of the personal matching unit 50. Additionally, the blood sugar level processing unit 60 may also generate dietary control, exercise, and life pattern regulation information of the activity which allow the blood sugar level of the user to be more effectively regulated to a blood sugar level matched with the user-specific blood sugar amount integrated information based the life pattern bio information sensed by the sensing unit 10.

The blood sugar level processing unit 60 may judge to which state or situation the motion of the user corresponds by comparing the motion sensing information sensed by the sensing unit 10 with predetermined motion standard model information in order to generate the life pattern regulation information. The blood sugar level processing unit 60 may judge to which state or situation the motion of the user corresponds by comparing the motion sensing information sensed by the sensing unit 10 with predetermined motion standard model information in order to generate the life pattern regulation information.

In addition, the blood sugar level processing unit 60 may generate the life pattern regulation information according to the judged state information of the user. As an example, when the judged motion sensing information and body information are compared with motion standard model information and body information standard model information, if it is judged that an arm moves during eating and food is being taken, life pattern regulation information for the eating end may be generated or life pattern regulation information for maintaining continuous food taking may be generated.

The output unit 70 outputs the matching result of the personal matching unit 50 provided by the blood level processing unit 60 to the outside to be recognized externally. Further, the output unit 70 may additionally output the life pattern regulation information generated by the blood sugar level processing unit 60 to the outside to be recognized externally. In this case, when the output unit 70 is the wrist wearing type, the output unit 70 may also output the life pattern regulation information so as for the user to recognize the life pattern regulation information visually, acoustically, and/or tactually through at least one of the display, a speaker, and a vibrator.

As an example, in order to lose the weight, in respect to a visual output, by applying a color signal lamp, a blood sugar level at which the weight is lost is displayed with a green at 70 mg/dl or more to less than 100 mg/dl based on the fasting blood sugar, a blood sugar level at which the weight is not significantly lost after eating is displayed with a yellow at 100 mg/dl or more to less than 140 mg/dl, and a blood sugar level at which a large weight may be gained is displayed with a red at 140 mg/dl or more. However, it may be additionally displayed that there is the possibility of diabetes at 200 mg/dl or more.

However, in order to gain the weight, the green and the red may be set to be displayed opposite to each other by the increase and decrease information input by the input unit 30, but the present invention is not limited thereto.

Therefore, a user who aims at losing the weight decreases carbohydrate-oriented food that increases a high blood sugar level as the color signal lamp is changed according to the blood sugar level and intakes the food, and maintains the color signal lamp not to be changed from the green to the red, while maintaining the green as possible for a lot of time during one day.

As an example, when the color signal lamp is changed to the red, the intake of the food is stopped, and the blood sugar level is guided to be decreased by intake of only a drink with no calorie, such as water, etc., or a motion such as walking, strolling, etc., after eating. For reference, the blood sugar may be reduced by 10 to 20% only by walking for 10 minutes after eating. Further, if the blood sugar is raised due to intake of a snack in addition to a meal, and the color signal lamp is thus displayed with the yellow, the activity may be increased so that the blood sugar level is decreased to the green showing the fasting blood sugar again within a short time.

Further, when the blood sugar is more rapidly raised after intake of specific food and the color signal lamp is more rapidly changed to the red, the weight gaining and obesity may also be prevented by a method for intentionally avoiding the intake of the food afterwards.

The battery unit 80 supplies power to actuate and drive the sensing unit 10, the storage unit 20, the input unit 30, the blood sugar measurement unit 40, the personal matching unit 50, the blood sugar level processing unit 60, and the output unit 70. The battery unit 80 may include, a rechargeable battery, a battery, a solar cell, etc.

The method for obesity prevention and weight regulation using noninvasively measuring blood sugar according to the present invention configured as such will be described in detail as follows. The same reference numerals as those in FIGS. 1 to 2 refer to the same members performing the same function.

Prior to the description, blood sugar amount integrated information used for the obesity prevention and the weight regulation by matching the blood sugar level of the user is a numerical value calculated by considering a correlation of food intake, the blood sugar, and insulin.

Specifically, in a normal person (without diabetes), the fasting blood sugar is 70 to 100 mg/dl and postprandial blood sugar is up to 200 mg/dl, and when the blood sugar is equal to or more than 70 to 100 mg/dl and 200 mg/dl, diabetes is diagnosed, and in the case of the normal person, the blood sugar starts to increase within 10 minutes after the food intake and the blood sugar is restored to normal blood sugar (less than 140 mg/dl) within 2 to 3 hours, and during this process, the insulin works.

Here, one point is that in the case of the normal person without diabetes, the blood sugar is not decreased to less than 70, and in such a phenomenon, when the blood sugar is decreased to a predetermined level or less, use of glucose (glycogen) in which catabolic hormone such as glucagon is secreted and stored, and gluco-neogenesis through steatolysis are caused and the blood sugar is thus raised, and this process may prevent fatal hypoglycemic shock.

Referring to such a process, if blood sugar approximately in a state of not going to the hypoglycemic shock is continuously maintained and a blood level (within a maximum of 100 to 140 mg/dl) approximately in a degree of not causing rapid insulin secretion even after eating is maintained, a reduction effect of body fat and the weight may be efficiently obtained, and on the contrary, when the weight is gained or the weight should be obtained for a health reason, if a blood sugar level (100 to 140 mg/dl) at a degree of not damaging pancreas may be maintained for a predetermined time or more by the rapid insulin secretion, a desired weight gaining effect may be obtained by an anabolic effect of insulin.

In the present invention, an object of obesity prevention and weigh regulation is enabled to be achieved, which is scientific and efficient, and does not damage the body by comparing the blood sugar amount integrated information set according to such a criterion with the measured blood sugar level. That is, the invention of the present invention is applicable only to the normal person, so when there is already diabetes and there is a problem in insulin secretion or in-body insulin sensitivity, insulin secretion restraint or promotion by the present invention causes hypoglycemia and hyperglycemia shock, and as a result, it may be dangerous. Therefore, the invention may not be applied.

Figure 3:
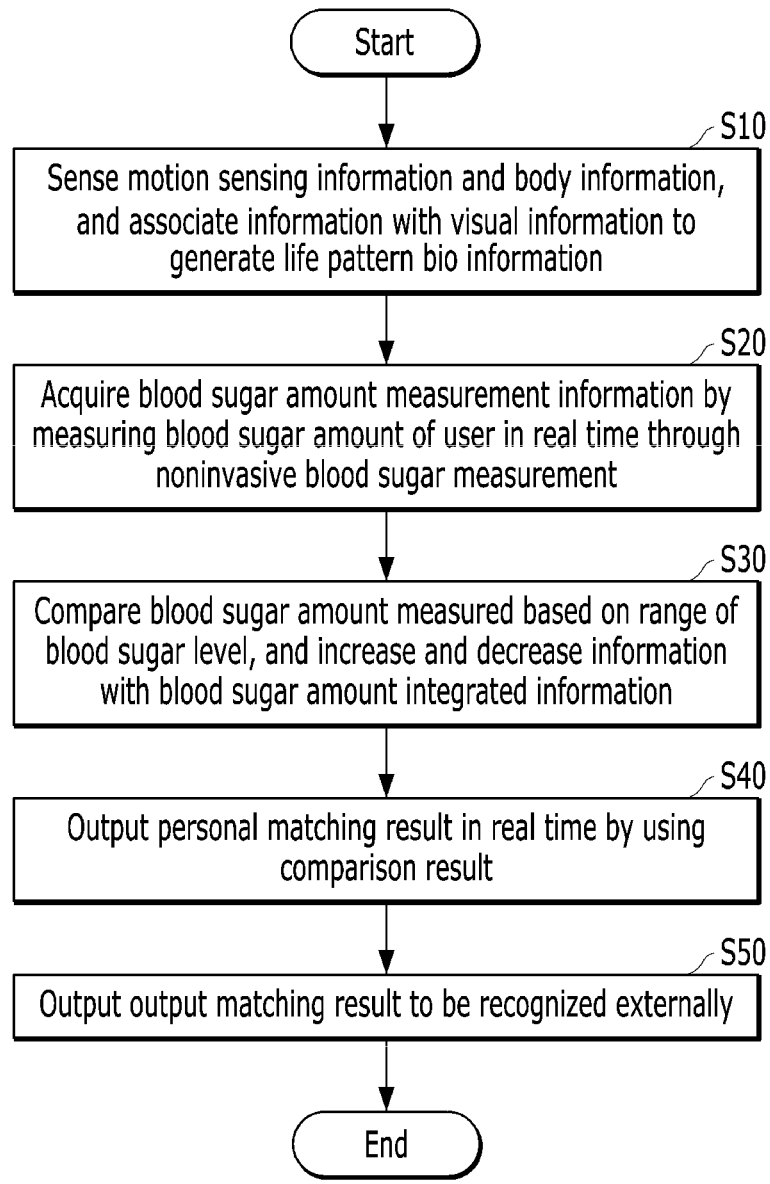
FIG. 3 is a flowchart for describing a method for obesity prevention and weight regulation using noninvasively measuring blood sugar according to an embodiment of the present invention.

FIG. 3 is a flowchart for describing a method for obesity prevention and weight regulation using noninvasively measuring blood sugar according to an embodiment of the present invention.

In this case, the method for obesity prevention and weight regulation using noninvasively measuring blood sugar according to the present invention may be operated through constitution of the sensing unit 10, the storage unit 20, the input unit 30, the blood sugar measurement unit 40, the personal matching unit 50, the blood sugar level processing unit 60, the output unit 70, and the battery unit 80 provided in a wearable type obesity prevention and weight regulation apparatus worn on the body of the user.

When described by referring to FIG. 3, first, motion sensing information and body information are sensed by using the sensing unit 10, and the information is associated with visual information to generate life pattern bio information (S10).

In this case, the motion sensing information as information acquired by sensing a motion of a user's arm by using a gyro or acceleration sensor is information through which an activity depending on a physical motion of the user, such as eating, sleeping, or exercise may be judged. Further, the body information as information acquired by sensing a body temperature, a heart rate, blood oxygen saturation, etc., of the user by using a heart rate pulse sensor, a body temperature sensor, a blood oxygen saturation sensor, a GPS sensor, etc., refers to information regarding a health state of the body.

In addition, the blood sugar amount information is acquired by measuring the blood sugar amount of the user in real time using noninvasively measuring blood sugar by using the blood sugar measurement unit 40 (S20). In this case, the blood sugar amount measurement information as information acquired by measuring the blood sugar amount of the user by the blood sugar measurement unit 120 refers to information including a blood sugar measurement time and a blood sugar amount measurement value. In addition, the blood sugar amount measurement value acquired through the measurement is associated with the blood sugar measurement time to generate the blood sugar amount measurement information. Here, the blood sugar measurement time refers to a time of measuring the blood sugar amount.

Subsequently, the blood sugar amount measured by the blood sugar measurement unit 40 is compared with the blood sugar amount integrated information stored in the storage unit 20 based on a range of a blood level, and increase and decrease information, which are input by the input unit 30 or are predetermined by using the personal matching unit 50 (S30).

In this case, the range of the blood sugar level may include a range of a blood sugar level (fasting blood sugar) at which the weight is lost for each person, which is stored in the storage unit 20, a range of a blood sugar level at which the weight is not significantly gained, and a range of a blood sugar level at which a large weight may be gained by rapid insulin secretion. In addition, the increase and decrease information may include information selected to select and regulate gaining or losing the weight by the user.

A user-specific matching result is output in real time by using a matching result of the personal matching unit 50 by using the blood sugar level processing unit 60 (S40). Additionally, the blood sugar level processing unit 60 may also generate dietary control, exercise, and life pattern regulation information of the activity which allow the blood sugar level of the user to be more effectively regulated to a blood sugar level matched with the user-specific blood sugar amount integrated information based the life pattern bio information sensed by the sensing unit 10.

Figure 4:
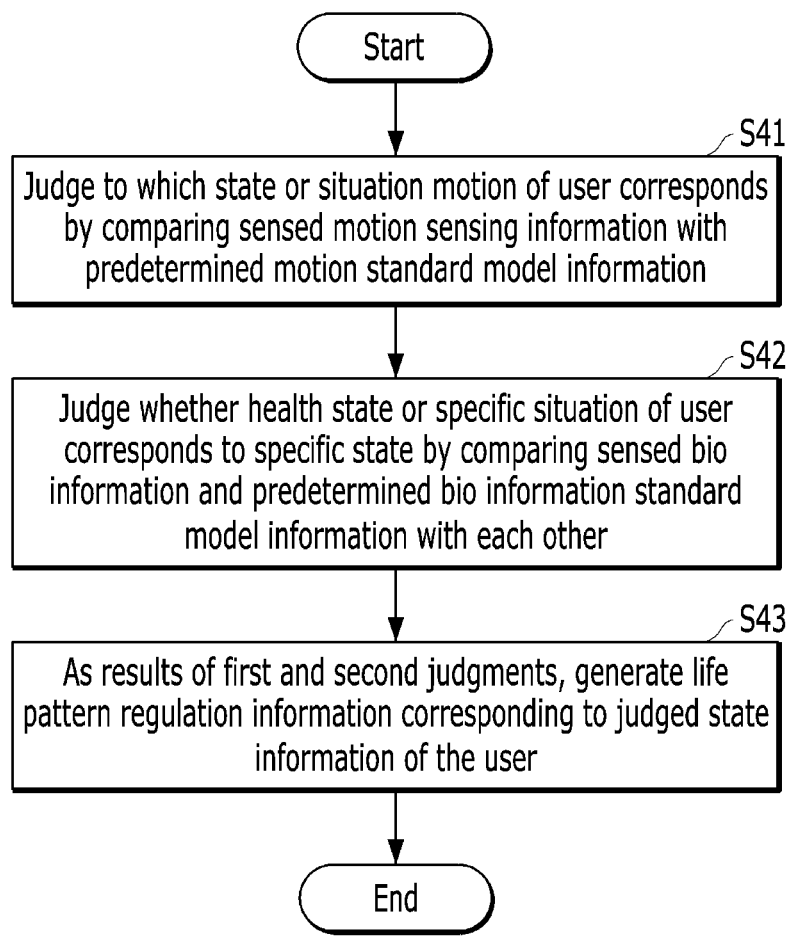
FIG. 4 is a flowchart for describing a process of generating life pattern regulation information by a blood sugar level processing unit of FIG. 3.

FIG. 4 is a flowchart for describing a process of generating life pattern regulation information by a blood sugar level processing unit of FIG. 3.

When described by referring to FIG. 4, it is judged to which state or situation the motion of the user corresponds by comparing the motion sensing information sensed by the sensing unit 10 with predetermined motion standard model information in order to generate the life pattern regulation information (first judgment) (S41).

In addition, the bio information sensed by the sensing and predetermined bio information standard model information are compared with each other to judge whether a health state or situation corresponds to whether the food being taken or a specific state such as sauna, sleep, etc. (second judgment) (S42).

As results of the first and second judgments, life pattern regulation information corresponding to the judged state information of the user is generated (S43).

As an example, when the judged motion sensing information and body information are compared with motion standard model information and body information standard model information, if it is judged that an arm moves during eating and food is being taken, life pattern regulation information for the eating end may be generated or life pattern regulation information for maintaining continuous food taking may be generated.

Subsequently, the matching result of the personal matching unit 50 provided by the blood level processing unit 60 is output to the outside to be recognized externally by using the output unit 70 (S50). Additionally, the output unit 70 may additionally output the life pattern regulation information generated by the blood sugar level processing unit 60 to the outside to be recognized externally.

In this case, when the output unit 70 is the wrist wearing type, the output unit 70 may also output the life pattern regulation information so as for the user to recognize the life pattern regulation information visually, acoustically, and/or tactually through at least one of the display, a speaker, and a vibrator.

In the output unit 70, the display continuously displays, and may announce the user (wearer) to recognize that the color of the color signal lamp is changed through vibrator and/or the speaker at the time when the color signal lamp is changed. However, a motion relationship among the display, the speaker, and the vibrator is just one example, but is not limited thereto, and various examples will be possible.

As an example, in order to lose the weight, in respect to a visual output, by applying a color signal lamp, a blood sugar level at which the weight is lost is displayed with a green at 70 mg/dl or more to less than 100 mg/dl based on the fasting blood sugar, a blood sugar level at which the weight is not significantly lost after eating is displayed with a yellow at 100 mg/dl or more to less than 140 mg/dl, and a blood sugar level at which a large weight may be gained is displayed with a red at 140 mg/dl or more. However, it may be additionally displayed that there is the possibility of diabetes at 200 mg/dl or more.

However, in order to gain the weight, the green and the red may be set to be displayed opposite to each other by the increase and decrease information input by the input unit 30, but the present invention is not limited thereto.

Therefore, a user who aims at losing the weight decreases carbohydrate-oriented food that increases a high blood sugar level as the color signal lamp is changed according to the blood sugar level and intakes the food, and maintains the color signal lamp not to be changed from the green to the red, while maintaining the green as possible for a lot of time during one day.

As an example, when the color signal lamp is changed to the red, the intake of the food is stopped, and the blood sugar level is guided to be decreased by intake of only a drink with no calorie, such as water, etc., or a motion such as walking, strolling, etc., after eating. For reference, the blood sugar may be reduced by 10 to 20% only by walking for 10 minutes after eating. Further, if the blood sugar is raised due to intake of a snack in addition to a meal, and the color signal lamp is thus displayed with the yellow, the activity may be increased so that the blood sugar level is decreased to the green showing the fasting blood sugar again within a short time.

On the contrary, when a user who intends to gain the weight and to be fatten may continuously maintain a yellow signal lamp (100 to 140 mg/ld) or more, which is blood sugar at a level at which the insulin secretion is increased without damage for a predetermined time during a day, an anabolic situation is maintained by continuous supply of insulin, and as a result, the user may be fatten. That is, when the color signal lamp becomes green and the blood sugar decreases, a method for raising the green to the yellow again by taking a small amount of food may be used.

Additionally, the output unit 70 may generate an output so as to enable the user to recognize the blood sugar visually, acoustically, or/and tactually through at least one of the display, the speaker, and the vibrator, and as a result, if the output unit 70 guides screen staring by a method such as vibration or sound at the time when the color signal lamp is changed (green to yellow, or yellow to red, or in a reverse case), more efficient regulation will be possible.

Meanwhile, the devices according to the disclosed embodiment may include a processor, a memory storing and executing program data, a permanent storage such as a disk drive, a communication port communicating with an external apparatus, a user interface device such as a touch panel, a key, a button, etc., and the like. Methods implemented by a software module or algorithm as computer-readable codes or program commands executable on the processor may be stored in computer-readable recording media. The media are readable by a computer, stored in the memory executable by the processor.

All documents including an opened document, a patent application, a patent, etc., cited in the disclosed embodiment may be merged into the disclosed embodiment in the same manner as those individually and specifically merged and represented by each cited document or those totally merged and represented in the disclosed embodiment.

For understanding of the disclosed embodiment, reference numerals are described in the preferred embodiments shown in the drawing, and specific terms are used to describe the disclosed embodiment, but the embodiments disclosed by the specific terms are not limited, and the disclosed embodiment may include all components that those skilled in the art may generally consider.

The disclosed embodiment may be represented by functional block components and various processing steps. The functional blocks may be implemented by various numbers of hardware or/and software components executing specific functions. For example, the disclosed embodiment may adopt integrated circuit components including a memory, processing, logic, a look-up table, etc., which may execute various functions by control by one or more microprocessors or by other control devices. Similarly to a case where the component of the disclosed embodiment may be executed by software programming or software elements, the disclosed embodiment includes a data structure, processes, routines, or various algorithms implemented by a combination of other programming components to be implemented by a programming or scripting language such as C, C++, Java, assembler, etc. Functional aspects may be implemented by an algorithm executed by one or more processors. Further, the disclosed embodiment may adopt related art for electronic environmental setting, signal processing, and/or data processing. Terminologies such as "mechanism", "element", "means", and "component" may be widely used, and are not limited to mechanical and physical components. The terminologies may mean a meaning of a series of routines of software in link with a processor, etc.

Specific executions described in the disclosed embodiment are exemplary embodiments and the scope of the exemplary embodiment is not limited even by any method. For brevity of the specification, descriptions of conventional electronic configurations, control systems, software, and other functional aspects of the systems may be omitted. Further, connection or connection members of lines among components exemplarily represent functions connections and/or physical or circuitry connections and may be represented as various functional connections, physical connections, or circuitry connections which are replaceable or added in an actual device. Further, unless otherwise specified, such as "essential", "important", etc., the connections may not be components particularly required for application of the disclosed embodiment.

Further, it will also be appreciated by those skilled in the art that various embodiments can be made within the scope of the technical spirit of the present invention. Accordingly, the true technical scope of the present invention should be defined by the technical spirit of the appended claims.

EXPLANATION OF REFERENCE NUMERALS AND SYMBOLS

10: Sensing unit
20: Storage unit
30: Input unit
40: Blood sugar measurement unit
50: Personal matching unit
60: Blood sugar level processing unit
70: Output unit
80: Battery unit

The invention claimed is:

1. A wearable apparatus for obesity prevention and weight regulation using noninvasively measured blood sugar, the wearable apparatus consisting of:
   a sensing unit being configured to be attached to a user and sensing motion sensing information and body information of the user to generate life pattern bio information;
   a storage unit storing the life pattern bio information including the motion sensing information and the body information generated by the sensing unit, storing motion standard model information to be compared so as to judge a state of the user by comparing with the motion sensing information, and storing blood sugar amount measurement information including an acquired blood sugar amount measurement value and blood sugar amount integrated information to be compared so as to judge a blood sugar level corresponding to weight gaining or losing for each user by comparing the blood sugar amount measurement information,
   wherein the blood sugar amount integrated information associated with the obesity prevention and the weight regulation is preset to include
      a weight-loss blood sugar level which is between 70 mg/dl or more and less than 100 mg/dl based on a fasting blood sugar,
      a post-meal blood sugar level which is between 100 mg/dl or more and less than 140 mg/dl based on a post-meal blood sugar, and a weight-gain blood sugar level which is 140 mg/dl or more;
an input unit configured to receive predetermined information from the user so as for the user to selectively set a range of the blood sugar level;
a blood sugar measurement unit measuring a blood sugar amount in real time through noninvasive blood sugar measurement to acquire the blood sugar amount measurement information;
a personal matching unit, based on the set range of the blood sugar level from the input unit, comparing the blood sugar amount in real time measured by the blood sugar measurement unit with the blood sugar amount integrated information stored in the storage unit;
a blood sugar level processing unit outputting a personal matching result in real time by using a comparison result of the personal matching unit,
wherein the blood sugar level processing unit generates life pattern regulation information based on the life pattern bio information sensed by the sensing unit; and
an output unit outputting the personal matching result output by the blood sugar level processing unit to the outside to be recognized externally via a color through a display, a sound through a speaker, and a vibration through a vibrator,
wherein the color includes a green, a yellow, and a red so that upon the green changes to yellow, the yellow changes to the red, or in a reverse case, the sound or the vibration is operated at the same time,
wherein the green indicates the weight-loss blood sugar level, the yellow indicates the post-meal blood sugar level, and the red indicates the weight-gain blood sugar level,
wherein, in a weight loss mode, the output unit outputs the green to instruct the user to intake a food and the red to instruct the user to stop intake the food for the obesity prevention,
wherein, in a weight gain mode, the output unit outputs the green and the red set to be displayed opposite to each other, wherein the green is outputted by the output unit to instruct the user to intake the food for the weight regulation including the weight gain.

2. A method for obesity prevention and weight regulation using noninvasively measured blood sugar of a user, the method consisting of:
sensing, by a sensing unit attached to the user, motion sensing information and body information and associating the information with visual information to generate life pattern bio information of the user;
storing, by a storage unit, the life pattern bio information including the motion sensing information and the body information generated by the sensing unit, storing prede termined motion standard model information to be compared so as to judge a state of the user by comparing with the motion sensing information, and storing blood sugar amount measurement information including an acquired blood sugar amount measurement value and blood sugar amount integrated information to be compared so as to judge a blood sugar level corresponding to weight gaining or losing for each user by comparing the blood sugar amount measurement information,
wherein the blood sugar amount integrated information associated with the obesity prevention and the weight regulation is preset to include a weight-loss blood sugar level which is between 70 mg/dl or more and less than 100 mg/dl based on a fasting blood sugar,
a post-meal blood sugar level which is between 100 mg/dl or more and less than 140 mg/dl based on a post-meal blood sugar, and
a weight-gain blood sugar level which is 140 mg/dl or more;
inputting, by an input unit, a predetermined information from the user so as for the user to selectively set a range of the blood sugar level;
measuring, by a blood sugar measurement unit, a blood sugar amount in real time through noninvasive blood sugar measurement to acquire the blood sugar amount measurement information;
based on the set range of the blood sugar level, comparing, by a personal matching unit, the blood sugar amount measured in real time by the blood sugar measurement unit with the blood sugar amount integrated information stored in the storage unit;
outputting, by a blood sugar level processing unit, a personal matching result in real time by using a comparison result of the personal matching unit, wherein the blood sugar level processing unit generates life pattern regulation information based on the life pattern bio information sensed by the sensing unit; and
outputting, by an output unit, the personal matching result to the outside to be recognized externally via a color through a display, a sound through a speaker, and a vibration through a vibrator,
wherein the color includes a green, a yellow, and a red so that upon the green changes to yellow, the yellow changes to the red, or in a reverse case, the sound or the vibration is operated at the same time,
wherein the green indicates the weight-loss blood sugar level, the yellow indicates the post-meal blood sugar level, and the red indicates the weight-gain blood sugar level,
wherein, in a weight loss mode, the output unit outputs the green to instruct the user to intake a food and the red to instruct the user to stop intake the food for the obesity prevention,
wherein, in a weight gain mode, the output unit outputs the green and the red set to be displayed opposite to each other, wherein the green is outputted by the output unit to instruct the user to intake the food for the weight regulation including the weight gain.

3. The method for obesity prevention and weight regulation using noninvasively measuring blood sugar of claim 2, wherein the step of outputting the personal matching result further consists of a first judgment step of judging to which state or situation motion of the user corresponds by comparing the motion sensing information sensed by the sensing unit with the predetermined motion standard model information, a second judgment step of judging whether a health state or a specific situation of the user corresponds to a specific state by comparing the information sensed by the sensing unit and predetermined information standard model information with each other, and as results of the first and second judgments, generating the life pattern regulation information of the user.

* * * * *